United States Patent [19]

Elgavish

[11] Patent Number: 5,804,164
[45] Date of Patent: Sep. 8, 1998

[54] WATER-SOLUBLE LIPOPHILIC CONTRAST AGENTS

[75] Inventor: Gabriel A. Elgavish, Hoover, Ala.

[73] Assignee: Research Corporation Technologies, Inc., Tucson, Ariz.

[21] Appl. No.: 615,661

[22] Filed: Mar. 13, 1996

[51] Int. Cl.⁶ .................................................. A61B 5/055
[52] U.S. Cl. ............................. 424/9.364; 424/9.365; 556/50; 556/55; 556/63; 556/77; 556/105; 556/116; 556/134; 556/148; 534/16; 560/169; 514/492; 514/502; 514/558; 514/563; 514/836
[58] Field of Search .................... 514/492, 502, 514/558, 563, 836; 436/173; 128/653.4, 654; 534/16; 556/50, 55, 63, 77, 105, 116, 134, 148; 560/169; 424/9.364, 9.365

[56] References Cited

U.S. PATENT DOCUMENTS

| | | | |
|---|---|---|---|
| 4,387,087 | 6/1983 | Deutsch | 424/1.5 |
| 4,489,054 | 12/1984 | Deutsch | 424/1.5 |
| 4,647,477 | 3/1987 | Gries et al. | 424/9 |
| 4,687,658 | 8/1987 | Quay | 424/9 |
| 4,687,659 | 8/1987 | Quay | 424/9 |
| 4,746,507 | 5/1988 | Quay | 424/9 |
| 4,804,529 | 2/1989 | Bardy et al. | 424/9 |
| 4,822,594 | 4/1989 | Gibby | 424/9 |
| 5,154,914 | 10/1992 | Elgavish | 424/9 |
| 5,242,681 | 9/1993 | Elgavish | 424/4 |
| 5,370,860 | 12/1994 | Elgavish | 424/4 |
| 5,460,799 | 10/1995 | Elgavish | 424/9.364 |
| 5,531,978 | 7/1996 | Berg et al. | 424/1.11 |

FOREIGN PATENT DOCUMENTS

| | | |
|---|---|---|
| 0 169 299 A2 | 1/1986 | European Pat. Off. . |
| 0 299 795 A1 | 1/1989 | European Pat. Off. . |
| 91/14178 | 9/1991 | WIPO . |

OTHER PUBLICATIONS

Kim, et al., "Fatty–Acyl Iminopolycarboxylates: Lipophilic Bifunctional Contrast Agents for NMR Imaging," Magnetic Resonance in Medicine, vol. 22, pp. 57–67 (Nov. 1991).

Kim, et al., "Gadolinium Complexes of [(Myristoyloxy)propyl]diethylenetriaminetetraacetate: New Lipophilic, Fatty Acyl Conjugated NMR Contrast Agents," Bioconjugate Chem., vol. 3, pp. 20–26 (1992).

Simor, et al., "In Vivo MRI Visualization of Acute Myocardial Ischemia and Reperfusion in Ferrets by the Persistant Action of the Contrast Agent Gd(BME–DTTA)," Circulation, vol. 92, No. 12, pp. 3549–3559 (Dec. 15, 1995).

Karesh, et al. (1977) J. Pharm. Sci. 66:225–228.

*Primary Examiner*—Gary E. Hollinden
*Attorney, Agent, or Firm*—Scully, Scott, Murphy & Presser

[57] ABSTRACT

The present invention relates to water-soluble, lipophilic contrast-enhancing agents, pharmaceutical compositions thereof and methods for diagnostic analysis, particularly NMR or MRI analysis using these contrast-enhancing agents. The water-soluble, lipophilic contrast-enhancing agents are chelates of a paramagnetic, ferromagnetic or diamagnetic metal ion(s) complexed with completing acids which contain at least one short-chain fatty acyl moiety having from about 0 to about 6 carbon atoms in its structure.

42 Claims, 4 Drawing Sheets

WATER-SOLUBLE LIPOPHILIC CONTRAST AGENTS

FIELD OF THE INVENTION

The loss of detail in NMR spectra or lack of sufficient contrast in NMR images can oftentimes limit the use of NMR analysis. Contrast-enhancing agents have been employed in the prior art in order to improve NMR imaging for non-invasive clinical diagnoses of mammalian hosts. The present invention relates to a class of compositions and to a method for NMR imaging using NMR signal affecting amounts of a paramagnetic, diamagnetic or ferromagnetic metal ion chelated with a ligand to yield a novel water-soluble, lipophilic contrast-enhancing agent. Moreover, the water-soluble, lipophilic compositions of the present invention are useful for X-ray image analysis and in ultrasonic contrast analysis.

BACKGROUND OF THE INVENTION

Diagnostic imaging has emerged in recent years as a powerful technique for noninvasive clinical diagnosis of the heart, brain, kidney as well as other organs and tissues in mammalian hosts. Nuclear magnetic resonance (NMR) analysis, or magnetic resonance imaging (MRI), in many instances, requires contrast enhancement to obtain useful spectra or images which delineate various aspects of the tissue, especially normal as contrasted with abnormal or diseased tissue.

The techniques of MRI or NMR spectroscopy encompass the detection of certain atomic nuclear spins utilizing magnetic fields and radio-frequency radiation. It is similar in some respects to X-ray computed tomography (CT) in providing a cross-sectional display of the body organ anatomy with excellent resolution of soft tissue detail. In current use, the images produced constitute a map of the distribution density of protons or other nuclei and/or their relaxation times in organs and tissues. The MRI technique is advantageously non-invasive as it avoids the use of ionizing radiation.

The prior art discloses various techniques that can be employed for affecting an NMR or MRI signal in a host, of which a common technique is to introduce into the host a paramagnetic substance prior to NMR or MRI analysis which advantageously affects MRI contrast, or selectively shifts the NMR signal. Accordingly, a large variety of compounds have been used in MRI, NMR and X-ray image analysis or as shift reagents.

New compounds with low toxicity in vivo, high relaxivity, tissue and pathology specificity, and sufficient tissue retention time but complete eventual clearance are being sought. The well known ethylenediaminetetraacetic acid (EDTA) and diethylenetriaminepentaacetic acid (DTPA) complexes with gadolinium (Gd) show low toxicity in vivo and rapid clearance rates but do not exhibit strong tissue specificity and long enough retention time, especially for myocardial tissue. Also their relaxivity decreases at high magnetic fields already being introduced into the industry. Accordingly, contrast-enhancing agents with higher relaxivity, positive field profile, greater tissue specificity and sufficient tissue retention time in addition to low toxicity are needed. One ongoing approach in the prior art is to modify EDTA and DTPA to achieve these goals.

U.S. Pat. No. 4,647,477 to Gries, et al. provides chelating agents for NMR analysis which include EDTA derivatives and DTPA derivatives differing significantly from the present invention since the chelating agents disclosed in Gries, et al. lack the short chain fatty acyl moiety of the subject invention and because of their inherently negative field profiles and their lack of tissue and pathology specificity.

Several additional EDTA and DTPA derivatives are disclosed in Quay U.S. Pat. Nos. 4,687,658; 4,687,659; 4,746,507; U.S. Pat. No. 4,804,529 to Bardy, et al. and U.S. Pat. No. 4,822,594 to Gibby. Collectively, the foregoing patents report ester, amide and polysaccharide derivatives which are suitable for general MRI analysis but which, nevertheless do not have the water-solubility and positive field profiles of the present contrast-enhancing agents.

In a study of the biological distribution of chemical analogs of fatty acids and long chain hydrocarbons containing a strong chelating agent, Karesh, S. M., et al. (1977) *J. Pharm. Sci.* 66:225–228, describes radiopharmaceutical cobalt (Co) and technecium (Tc) complexes wherein the alkyl end of a fatty acid molecule is covalently bound to a carboxyl group on the chelating agent, forming an ester derivative of the chelating agent. Moreover, Karesh, et al. reports that the compounds under investigation were not sufficient biological analogs to act as tracers for fatty acid metabolism in the myocardium.

Other useful lipophilic contrast-enhancing agents which have a lipophilic long chain fatty acid moiety are disclosed in U.S. Pat. Nos. 5,154,914; 5,242,681; 5,370,860 and 5,460,799 all to Elgavish, et al. Specifically, the contrast-enhancing agents disclosed in those Elgavish, et al. patents due to their insufficient water solubility need to be solubilized by liposomes in order to reach a functionally sufficient concentration which is useful in MRI imaging.

Other useful lipophilic contrast-enhancing agents are described in U.S. Pat. Nos. 4,387,087 and 4,489,054 both to Deutsch, et al. Specifically, the agents disclosed in the Deutsch, et al. patents are cationic lipophilic complexes of Tc-99m used in nuclear medicine and differ significantly from the agents of the present invention since no DTTA complexes or derivatives thereof are disclosed in those patents. Moreover, the agents disclosed in the Deutsch, et al. patents do not provide any magnetic effects and thus are irrelevant to the field of MRI and NMR.

Accordingly, the present invention provides lipophilic contrast-enhancing agents for diagnostic imaging analysis that are water-soluble in nature. In comparison to the agents in the previous Elgavish et al. patents, the present agents water solubility is rather unexpected considering that they have retained a characteristic which is rather contradictory to water-solubility, i.e. their lipophilicity. Despite their water-solubility, the contrast-enhancing agents of the present invention still show surprising high uptake and retention in myocardial tissue even without the need of any dispersing agents, such as liposomes. Thus, the present water-soluble, yet lipophilic a contrast-enhancing agents represent an improvement over prior art agents since the water-solubility property enhances the clinical practicality of the agents as well as eases its commercialization.

SUMMARY OF THE INVENTION

The present invention relates to water-soluble, lipophilic contrast-enhancing agents for diagnostic image analysis, preferably for NMR spectroscopy or MRI imaging, but which also find utility in X-ray image analysis and ultrasonic analysis. The term "contrast-enhancing agent" is used herein to denote an agent that has the ability to amplify the degree of difference in tone between the lightest and darkest areas of the organ or tissue that is being diagnosed or even create such an image contrast where one did not inherently exist before. While being generally described as contrast-enhancing agents herein, it is emphasized that the present agents described herein can also act as NMR shift reagents or agents that modify any other parameters relevant to NMR or MRI.

Specifically, the water-soluble, lipophilic contrast-enhancing agents of the present invention comprise a complexing acid, or a salt thereof, and at least one paramagnetic, diamagnetic or ferromagnetic metal ion, in any stoichiometric ratio between metal ions and complexing acids, with the complexing acid having the formula:

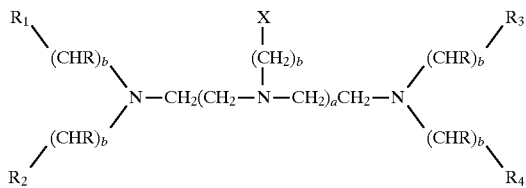

wherein a is 0 to 5; b is 1 to 5; each of a and b can be the same or different; each R is the same or different and is hydrogen, lower alkyl, hydroxy, halo, lower alkoxy, aryl, or lower aralkyl; at least one of $R_1$, $R_2$, $R_3$, $R_4$, or X is hydroxy or has the formula:

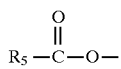

wherein $R_5$ is hydrogen or a saturated or unsaturated hydrocarbon chain having about 0 to about 6 carbon atoms; and the others of $R_1$, $R_2$, $R_3$, $R_4$, or X are hydrogen, hydroxyl, —$COOR_6$, —$CONR_7R_8$ or a chelating moiety, wherein $R_6$, $R_7$ and $R_8$ are the same or different and represent hydrogen, lower alkyl, lower alkoxy, lower carboxyalkylene, a saturated or unsaturated hydrocarbon chain having from about 1 to about 30 carbon atoms, or a chelating moiety.

The preferred water-soluble, lipophilic agents are those wherein the complexing acid has the formula:

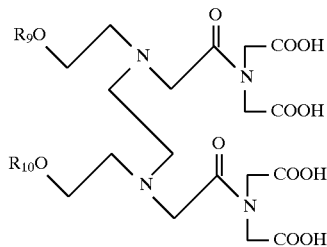

wherein $R_9$ is hydrogen or a short chain fatty acyl moiety of the formula:

wherein $R_{11}$ is hydrogen or a saturated or unsaturated hydrocarbon chain containing from about 0 to about 6 carbon atoms and $R_{10}$ is a fatty acyl moiety of the formula:

wherein $R_{12}$ is a saturated or unsaturated hydrocarbon chain having from about 1 to about 30 carbon atoms.

The most preferred compounds of the present invention which exhibit sufficient water solubility while retaining the necessary plateau-MRI kinetics, i.e. that the agent-induced effect in the MRI or NMR signals in tissue, e.g. the enhancement in myocardial proton MRI signal intensity, remains close to its plateau value for at least one hour after the agent has been administered, which is needed for imaging, are those compounds wherein the maximum length of $R_{11}$ is 3 or less and the minimum length of $R_{12}$ is 2 or more.

The above described water-soluble, lipophilic contrast-enhancing agents may be employed for noninvasive clinical diagnosis of the heart, brain, kidney as well as other organs and tissues in mammalian hosts. In a preferred embodiment, the water-soluble, lipophilic agents are employed for imaging myocardial tissue.

In another embodiment of the present invention, a method for diagnostic analysis of a host is provided. Specifically, this method comprises administering the aforementioned water-soluble, lipophilic contrast-enhancing agents to a host, preferably a mammalian host, in an amount sufficient to effect the desired contrast and then subjecting the host to diagnostic analysis. Preferably diagnostic analysis is NMR analysis; including and especially preferred, NMR imaging analysis (or MRI). Further, the subject compounds are also useful in diagnostic analysis by X-ray image analysis or ultrasonic analysis.

Another embodiment of the present invention relates to a method of tissue-specific imaging with a tissue-specific contrast-enhancing agent as provided herein.

The present invention also provides pharmaceutical compositions which comprise the above-mentioned water-soluble, lipophilic contrast-enhancing agents of the instant invention and a pharmaceutical acceptable carrier.

DETAILED DESCRIPTION OF THE INVENTION

Figure 1:
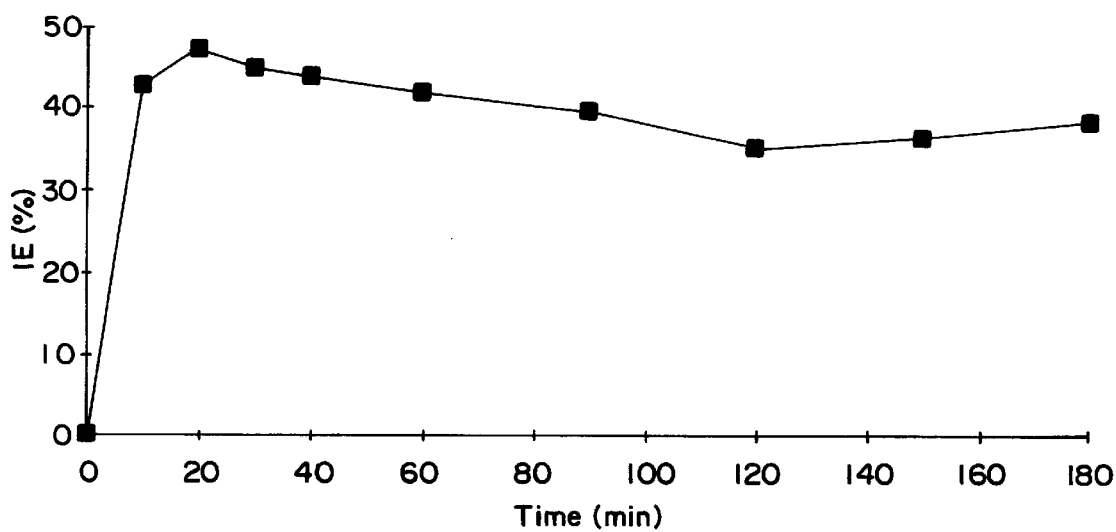
FIG. 1 is a graph of the myocardial proton MRI intensity enhancement, expressed in %, vs. time, expressed in minutes, utilizing Gd(ABE-DTTA) as the contrast-enhancing agent in an in vivo ferret experiment.

The present invention is directed to water-soluble, lipophilic contrast-enhancing agents which comprise a complexing acid or salt thereof and a paramagnetic, ferromagnetic or diamagnetic metal ion, in any stoichiometric ratio between the metal ion and the complexing acid, wherein the complexing acid or salt thereof has the formula:

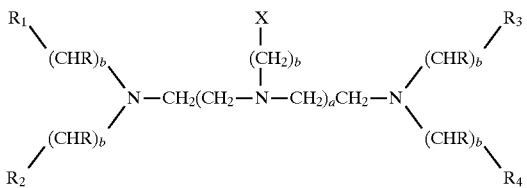

wherein a is 0 to 5; b is 1 to 5; each of a and b can be the same or different; each R is the same or different and is hydrogen, lower alkyl, hydroxy, halo, lower alkoxy, aryl, or lower aralkyl; at least one of $R_1$, $R_2$, $R_3$, $R_4$, or X is hydroxy or has the formula:

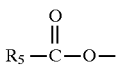

wherein $R_5$ is hydrogen or a saturated or unsaturated hydrocarbon chain having about 0 to about 6 carbon atoms; and the others of $R_1$, $R_2$, $R_3$, $R_4$, or X are hydrogen, hydroxyl, —$COOR_6$, —$CONR_7R_8$, or a chelating moiety, wherein $R_6$, $R_7$ and $R_8$ are the same or different and represent hydrogen, lower alkyl, lower alkoxy, lower carboxyalkylene, a saturated or unsaturated hydrocarbon chain having from about 1 to about 30 carbon atoms, or a chelating moiety.

The preferred water-soluble, lipophilic agents are those wherein the complexing acid has the formula:

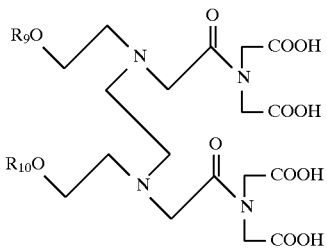

wherein $R_9$ is hydrogen or a short chain fatty acyl moiety of the formula:

wherein $R_{11}$ is hydrogen or a saturated or unsaturated hydrocarbon chain containing from about 0 to about 6 carbon atoms and $R_{10}$ is a fatty acyl moiety of the formula:

wherein $R_{12}$ is a saturated or unsaturated hydrocarbon chain having from about 1 to about 30.

It should be understood that $R_5$, $R_{11}$ and $R_{12}$ may be substituted or unsubstituted hydrocarbon chains. When $R_5$, $R_{11}$ and $R_{12}$ are substituted hydrocarbon chains, it is preferred that they be substituted with a lower alkyl, hydroxyl, lower alkoxy or halogen moiety. Of these substituents, it is most preferred if the hydrocarbon chain be substituted with a lower alkyl, e.g., methyl.

The term "salt" is used herein to denote that the completing acid may be ionically bonded to a metal ion from Groups IA or IIA of the Periodic Table of Elements.

The term "lipophilic" as used in the invention implies that the agents have a strong affinity for fats or fat-like material present in the organ or tissue being diagnosed, in particular in the hydrophobic composition of cell membranes to which the agents of the present invention may anchor with their lipophilic moiety, while still retaining their chelated metal ion accessible to the extracellular aqueous environment. The term "water-soluble" implies that the agents of the present invention are soluble in aqueous medium or environments in a concentration sufficient for the required NMR or MRI effect.

As used herein the term "completing acid" means an acid and may include a Lewis acid which acts as a ligand for the metal ion of interest thereby forming a chelate.

As used herein, the term lower alkyl, when used singly or in combination, refers to alkyl groups containing from about 1 to about 6, preferably 1 to about 4, carbon atoms. They may be straight chain or branched and include such groups as methyl, ethyl, propyl, isopropyl, butyl, sec-butyl, isobutyl, t-butyl, pentyl, isopentyl, neopentyl, hexyl and the like.

The term aryl, when used alone or in combination, refers to an aromatic ring containing from about 6 to about 10 carbon atoms. The aryl group includes phenyl, and 1- or 2-naphthyl. The preferred aryl is phenyl.

The term aralkyl refers to aryl groups as described above which have alkyl groups as ring substituents. The most preferred aralkyl group is benzyl.

The term lower carboxyalkylene refers to groups having the formula:

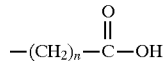

where n may vary from about 1 to about 5. Representative groups include, but are not limited to, carboxymethylene, carboxyethylene, carboxypropylene, carboxybutylene and carboxypentylene. The alkalene groups may, optionally, be branched. Especially preferred are carboxymethylene, carboxyethylene and carboxypropylene.

A chelating moiety is defined herein as any acidic group including groups from Lewis acids, capable of forming a complex with the metal ions of the present invention. Such moieties include carboxylic acids, phosphoric acids, amines and the like.

The term lower alkoxyl refers to a lower alkyl group having at least one hydroxyl substituent. This includes methoxy, ethoxy, propoxy, butoxy and the like. The term halogen refers to bromine, iodine, chlorine and fluorine.

The term saturated hydrocarbon refers to an alkyl chain which contains no double or triple bonds. Examples of such saturated hydrocarbon chains for use herein include, but are not limited to acetyl, propyryl, butyryl, myristyl, palmityl, lauryl, stearyl, caproyl, caprylyl, arachidyl, melissyl and the like. An unsaturated hydrocarbon chain contains at least one double bond or triple bond and may contain several of such bonds. Examples of unsaturated hydrocarbon chains as contemplated herein include, but are not limited to, oleyl, myristoleyl, palmitoleyl, elaidyl, linoleyl, arachidonyl, γ-linolenyl and the like.

The most preferred compounds of the present invention are those wherein $R_9$ is hydrogen or has the formula:

wherein $R_{11}$ is hydrogen or a saturated or unsaturated hydrocarbon having from about 1 to about 3 carbon atoms and wherein $R_{10}$ has the formula:

wherein $R_{12}$ is a saturated or unsaturated hydrocarbon chain having from about 3 to about 29 carbon atoms.

The especially preferred compounds of the present invention are N-(2-acetoyloxyethyl)-N'-(2-butyroyloxyethyl)-N,N'-bis[N",N"-bis(carboxylmethyl)-acetamido]-1,2 ethanediamine(ABE-DTTA), N-(2'-myristoyloxyethyl)-N'-(2'-hydroxyethyl) 1,8-dioxotriethylenetetraamine-N,N,N',N'-tetraacetic acid (MHE-DTTA), N,N'-bis(2-butyroyloxyethyl)-N,N'-bis [N",N"-bis(carboxylmethyl) acetamido]-1,2 ethanediamine (BBE-DTTA), N,N'-bis(2-propionoyloxyethyl)-N,N'-bis [N",N"-bis(carboxylmethyl) acetamido]-1,2 ethanediamine (BPE-DTTA), N-(2-propionoyloxyethyl)-N'-(2-butyroyloxyethyl)-N,N'-bis [N"N"-bis(carboxylmethyl)-acetamido]-1,2 ethanediamine (PBE-DTTA) and N,N'-bis(2-acetoyloxyethyl)-N,N'-bis[N",N"-bis(carboxylmethyl)acetamido]-1,2 ethanediamide (BAE-DTTA). Of these compounds, ABE-DTTA is most preferred.

The compounds of the present invention are prepared by art recognized methods. For example, compounds having acetamide substituents can be prepared by alkylating:

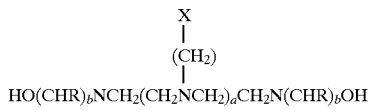

with a haloacetamide (with the acetamide group being substituted with an aralkyl carboxyalkylene if desirable) followed by monoaralkyloxycarbonylation on one of the hydroxyl groups and acylation of the other to obtain a monoacylated agent. Diacylation can be done directly after alkylation. In either case, the aralkyl groups of the carboxylates are removed by catalytic hydrogenation to obtain the complexing acid.

Other compounds of the invention represented by the formula:

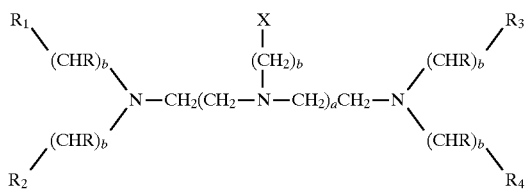

wherein $R_1$-$R_8$, X, a and b are as defined above, are also prepared by art recognized methods. For example, amino alcohols can be prepared by alkylation of:

with an alkyl halide, and then further alkylated with aralkyl halocarboxyalkylenes to obtain an intermediate

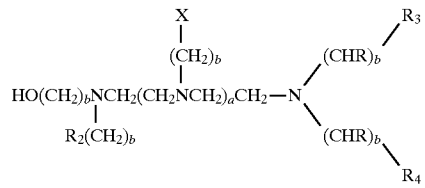

wherein X and $R_2$-$R_4$ are $COOR_{13}$ and $R_{13}$ is aralkyl (e.g. benzyl). The above compound can be acylated, preferably with an alkyl halide, followed by catalytic hydrogenation to remove the aralkyl groups and yield the desired compound. R groups can be introduced subsequent to the synthesis or by employing appropriately substituted alkylhalides or aralkyl halocarboxyalkylenes at the appropriate step. Moreover, similar production methods can be employed when the starting material is a compound of the formula:

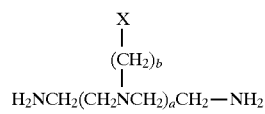

Alternately, a starting aminoalcohol of the formula:

can be alkylated with iodoacetamide to form a tertiary amine which can be subjected to reduction of the keto group and further alkylation with an aralkyl halocarboxyalkylene. Acylation and catalytic hydrogenation are then conducted as before, to yield the desired compounds.

An illustration of one synthetic route to prepare BBE-DTTA, PBE-DTTA, BPE-DTTA and ABE-DTTA, four of the preferred compounds of the instant invention, is shown in Scheme I below and is further exemplified in Example 1 (the compound numbers refer to those used in Example 1):

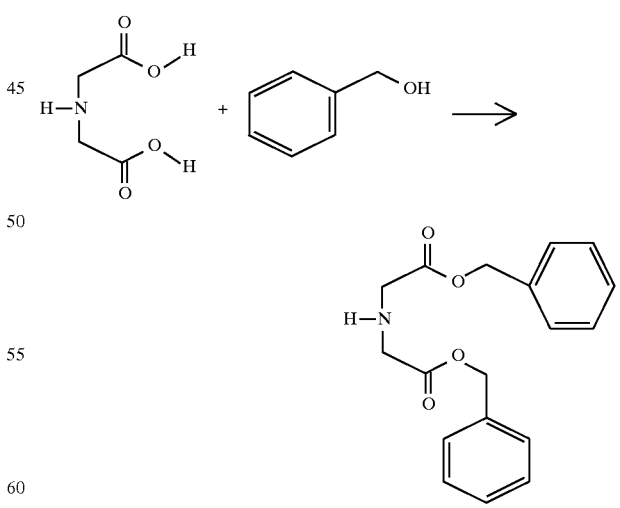

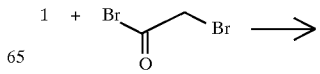

9
-continued
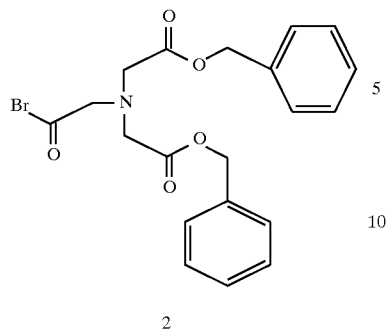
2
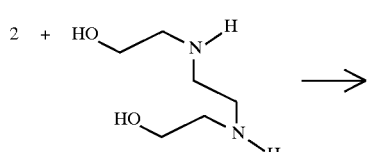
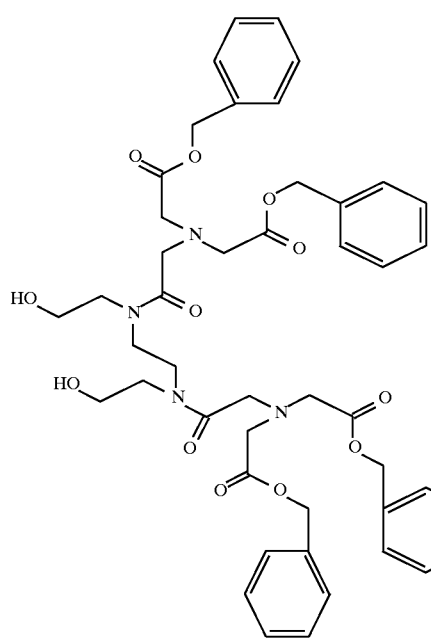
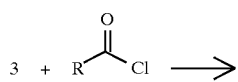
R = Methyl, Ethyl, Propyl
10
-continued
3
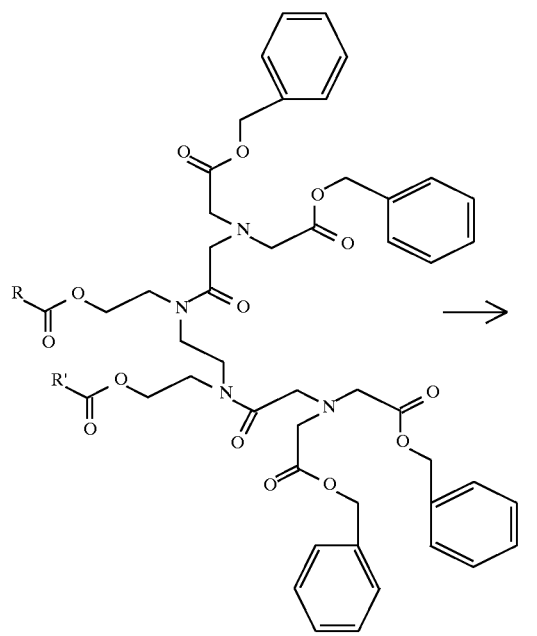
4. R = R' = Propyl
5. R = R' = Ethyl
6. R = Ethyl, R' = Propyl
7. R = Methyl, R' = Propyl
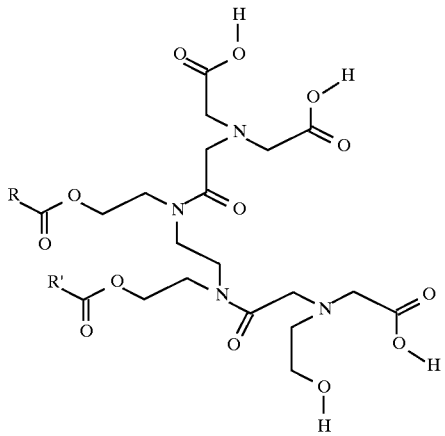
8. R = R' = Propyl
9. R = R' = Ethyl
10. R = Ethyl, R' = Propyl
11. R = Methyl, R' = Propyl The last step of the reaction scheme involves a catalytic hydrogenation step which employs 10% palladium on carbon, as the catalyst.

In addition to the complexing acid or salt thereof, the water-soluble, lipophilic contrast-enhancing agents of the present invention contain a metal ion selected from the group consisting of paramagnetic metal ions, diamagnetic metal ions, ferromagnetic metal ions, or X-ray absorptive metal ions.

For NMR or MRI, the preferred metal ions employed in the contrast-enhancing agent of the present invention are paramagnetic metal ions since metal ions of this type generally induce enhanced relaxation rates in the proton spins of the surrounding water molecules in a mammalian host where the agent is taken up, and generally produce the enhanced contrast results in mammalian hosts. Paramagnetic metal ions by definition are those metal ions that carry unpaired electrons.

Ferromagnetic metal ions may also be employed in this respect and include those metal ions whose internal magnetic moments spontaneously organize in a common direction.

Diamagnetic metal ions may also be employed in the present invention. The term diamagnetic metal ions is denoted herein as those metal ions that do not contain unpaired electrons. These metal ions position themselves at right angles to magnetic lines of force, and include for example, the alkaline earth metal ions (Group IIA of the Periodic Table of the Elements) and the alkali metal ions (Group IA of the Periodic Table of Element). The preferred alkaline earth metal ions comprise magnesium, calcium, strontium and barium whereas the preferred alkali metal ions comprise lithium, sodium and potassium.

The preferred paramagnetic metal ions comprise the metal ions from the lanthanide group of the Periodic Table of the Elements and comprise those metal ions having atomic numbers 57–70 inclusive, especially gadolinium and those metal ions having atomic numbers 21–29 inclusive, and 42–44 inclusive, especially copper, nickel, manganese, iron and chromium. Moreover, it is preferable that the metal ions be divalent or trivalent ions with suitable ions, for example, including chromium (III), manganese (II), iron (III), iron (II), colbalt (II), nickel (II), copper (II), praseodymium (III), neodymium (III), samarium (III) and ytterbium (III). Because of their very strong magnetic moments, gadolinium (III), terbium (III), dysprosium (III), holmium (III) and erbium (III) are preferred.

If the agents according to the invention are for use in X-ray diagnosis, the metal ion is derived from an element with a higher atomic number to achieve a sufficient absorption of X-rays. It has been found that contrast agents with metal ions of elements with atomic numbers of 57 to 83 inclusive are suitable for this purpose. These include, for example, lanthanum (III), the above mentioned ions of the lanthanide group, gold (III), lead (II) or, especially, bismuth (III).

All of the contrast-enhancing agents according to the invention, also intended for use both in NMR and X-ray diagnosis, are also suitable for use in ultrasonic diagnosis.

Production of the contrast agents is also known or can be performed fully conventionally as known in the art, e.g., in processes in which the metal oxide or a metal salt (for example, nitrate, chloride or sulfate) of an element with an atomic number of 21 to 29, 42 to 44 or 57 to 83 is dissolved or suspended in water and/or a lower alcohol (such as methyl, ethyl or isopropyl alcohol) and added to a solution or suspension of the equivalent amount of the complexing acid in water, a lower alcohol, or other suitable organic solvent (such as pyridine) and stirred, if necessary, with heating moderately or to the boiling point, until the reaction is completed. If the contrast agent that is formed is insoluble in the solvent that is used, it is isolated by filtering. If it is soluble, it can be isolated by evaporation of the solvent to dryness, for example, by spray drying.

If acid groups are still present in the resulting contrast agent, it is often advantageous to convert the acidic salt into a neutral salt by reaction with inorganic and/or organic bases or amino acids, which form physiologically biocompatible cations, and isolate them. In many cases, the procedure is even unavoidable since the dissociation of the complex salt is moved toward neutrality to such an extent by a shift in the pH value during the preparation that only in this way is the isolation of homogeneous products or at least their purification made possible. Neutralization is advantageously performed with organic bases or basic amino acids. It can also be advantageous, however, to perform the neutralization by means of inorganic bases (hydroxides, carbonates or bicarbonates) of sodium, potassium or lithium.

To produce the neutral salts, enough of the desired base can be added to the acidic contrast agents in an aqueous solution or suspension that the point of neutrality is reached. The resulting solution can then be concentrated to dryness in vacuo. It is often advantageous to precipitate the neutral salts by addition of solvents miscible with water, for example, lower alcohols (methyl, ethyl, isopropyl alcohols, etc.), lower ketones (acetones, etc.), polar ethers (tetrahydrofuran, dioxane, 1,2-dimethoxyethane, etc.) and thus obtain crystallizates that isolate easily and purify well. It has been found particularly advantageous to add the desired bases to the reaction mixture even during complexing and thus eliminate a process stage.

If the acidic contrast agent contains several free acid groups, it is then often advantageous to produce neutral mixed salts which contain both inorganic and organic physiologically biocompatible cations as counter ions. This can be done, for example, by reacting the complexing acids in an aqueous suspension or solution with the oxide or salt of the element supplying the metal ion and less than the full amount of an organic base necessary for neutralization, e.g., half, isolating the complex that is formed, purifying it, if desired, and then adding it to the amount of inorganic base necessary for complete neutralization. The sequence of adding the bases can also be reversed.

Another embodiment of the present invention is directed to a method for diagnostic analysis by administering the subject contrast-enhancing agents to a host, preferably a mammalian host, in an amount sufficient to effect the desired contrast (or shift, or other NMR or MRI effect) and then subjecting the host to diagnostic analysis. Preferably diagnostic analysis is NMR analysis; including and especially preferred, NMR imaging analysis (or MRI). Further, the subject compounds are useful in diagnostic analysis by X-ray image analysis or ultrasonic analysis. While described primarily as contrast-enhancing agents, the subject agents can also act as NMR shift reagents or as agents that induce a modification of any other parameters relevant to NMR or MRI and such use is contemplated by the methods herein.

The water-soluble, lipophilic contrast-enhancing agents of the present invention are administered in an amount sufficient to effect the desired contrast. For MRI, this amount is an MRI signal affecting amount of said agent, i.e., any amount of said agent that will alter the spin-lattice or spin-spin relaxation times of an MRI signal or for a shift reagent, selectively shift the spectral position of the signals of one or more resonant nuclei relative to other signals in the spectrum, or for an agent affecting other NMR or MRI relevant parameters, an amount sufficient to induce said effect. This alteration is effected in a manner in order to enhance the signals received from the specimen or host under analysis either by reducing the aforementioned relaxation times or by increasing them with respect to an area of the host or the host per se which has had the complex administered to it, or in order to enhance or reduce any parameter relevant to NMR or MRI. Shift reagents thus also provide distinction of signals in a specimen.

In another embodiment of the instant invention, the MRI signal affecting amount of the agent is that amount which in addition to changing the relaxation times of the MRI signals in the host, will also change such relaxation times sufficiently so that sharper lines of definition or higher contrast is obtained between those parts of the host tissue that have taken up a larger amount of the agent versus parts of the tissue that have taken up a smaller amount. Case in point, e.g., would be sufficient contrast generated between healthy heart muscle tissue which would take up normal amounts of the agent versus ischemic, underperfused heart muscle in diseased parts of the heart that would take up smaller amounts.

The relaxation time $T_1$ (called the spin lattice relaxation time) measures the rate at which magnetic energy is transferred from the resonant nuclei to all other energy degrees of freedom excluding other resonant nuclei. The relaxation time $T_2$ (spin-spin) measures the rate of magnetization transfer among resonant nuclei.

Another relevant parameter is the density ρ (rho) of the protons in the medium. As a first approximation, ρ represents the quantity of free water contained in the sample.

The image in nuclear magnetic resonance imaging represents the tissue distribution of these parameters ρ, $T_1$, $T_2$ or their combination. The contrast between the given tissue and the adjacent tissues increases as a function of the tissues containing more or less water or mobile protons and differing relaxation times. It is also possible to modify the contrast by artificially varying one or more of these parameters. Experience has shown that it was of greater interest to modify the relaxation time to improve the contrast of the image. This can be accomplished, for example, with contrast-enhancing agents provided herein. The density of the protons (in practice those of water and lipids) may or may not vary sufficiently among individual organs or between normal and pathological tissues. However, the relaxation characteristics are dependent on a larger number of factors (microscopic dynamics of the molecules, chemical exchange, paramagnetic disturbances, etc.), which are much more variable. The relative technical possibilities of selecting different parameters for obtaining the final image (experimentally magnetization echoes reflecting the function of $T_2$, or experimentally inversion-recovery or progressive saturation of the magnetization permitting the local measurement of $T_1$) have shown the significance of the method.

A detailed discussion of NMR or MRI, and theoretical considerations in selecting the appropriate parameters for diagnostic analysis is rendered in U.S. Pat. No. 4,749,560, which is incorporated herein by reference, e.g., CAT scans, X-ray image analysis and ultrasonic diagnosis are conducted in accordance with well-established techniques.

It should be emphasized herein that the present method of diagnostic analysis allows tissue- or organ-specific diagnostic analysis to be achieved without the need for utilizing conjugating agents which are typically required in prior art contrast-enhancing agents for ensuring maximum adsorption of the agent into the tissue or organ. Moreover, the subject water-soluble contrast-enhancing agents quite surprisingly and unexpectedly exhibit a sufficiently long tissue retention time reflected in their MRI kinetics behaving in a manner usually displayed only by lipophilic agents which are not soluble in aqueous media. They also, surprisingly and unexpectedly, exhibit organ and tissue specificity e.g., bidifferential distribution, especially in myocardial tissue without the need of requiring any dispersion agents, such as liposomes which are required in the previous Elgavish et al. patents. Hence, the present method which utilizes the inventive agents represents a significant improvement over prior art methods which require the use of dispersing agents.

The present water-soluble contrast agents may be administered to a host as a pharmaceutical composition in a contrast-enhancing amount. Specifically, the pharmaceutical composition contains a contrast-enhancing dosage of the contrast agents according to the invention together with a pharmaceutically acceptable carrier. The pharmaceutical compositions can be administered by well-known routes including oral, intravenous (if soluble) intramuscular, intranasal, intradermal, subcutaneous, parenteral, enteral and the like. Depending on the route of administration, the pharmaceutical composition may require protective coatings.

The pharmaceutical forms suitable for injectionable use include sterile aqueous solutions or dispersions and sterile powders for the extemporaneous preparation of sterile injectable solutions or dispersions. In all cases the ultimate solution form must be sterile and fluid. Typical pharmaceutical carriers include a solvent or dispersion medium containing, for example, water, buffered aqueous solutions (i.e., biocompatible buffers), ethanol, polyol (glycerol, propylene glycol, polyethylene glycol and the like), suitable mixtures thereof, surfactants or vegetable oils. Sterilization can be accomplished by any art recognized technique, including but not limited to, addition of antibacterial or antifungal agents, for example, paraben, chlorobutanol, phenol, sorbic acid, thimerosal and the like. Further, isotonic agents, such as sugars or sodium chloride may be incorporated in the pharmaceutical compositions of the present invention.

Production of sterile injectable solutions containing the subject water-soluble contrast agents is accomplished by incorporating these agents in the required amount in the appropriate solvent with various ingredients enumerated above, as required, followed by sterilization, preferably filter sterilization. To obtain a sterile powder, the above solutions are vacuum-dried or freeze-dried as necessary.

When the water-soluble contrast-enhancing agents of the present invention are administered orally, the pharmaceutical compositions thereof containing an effective dosage of the contrast agent, may also contain an inert diluent, an assimilable edible carrier and the like, be in hard or soft shelled gelatin capsules, be compressed into tablets, or may be in an elixir, suspension, syrup or the like.

The subject water-soluble contrast-enhancing agents are thus compounded for convenient and effective administration in pharmaceutically effective amounts with a suitable pharmaceutically acceptable carrier in a dosage which affects contrast enhancement. These amounts are preferably about 1 μmole to 1 mole of the contrast agent per liter and are administered in doses of about 0.001 to 5 mmole/kg body weight. Preferred compositions provide effective dosages of contrast agents in the range of about 0.001–5 mmole/kg; in the range of about 0.1–5 mmole/kg for X-ray diagnostics; and in the range of about 0.1–5 mmole/kg for ultrasound diagnostics.

As used herein, a pharmaceutically acceptable carrier includes any and all solvents, dispersion media, coatings, antibacterial and antifungal agents, isotonic agents and the like. The use of such media and agents are well known in the art.

The following examples further illustrate the invention.

EXAMPLE 1

Materials and Methods

High resolution protein NMR spectra to confirm intermediates and identify products, were recorded on a Bruker AM-360 instrument. Either $Me_4Si$ ($CDCl_3$, $DMSO-d_6$) or 3-(trimethylsilyl)-propionic acid-2,2,3,3-$d_4$ acid, sodium salt (TSP) ($D_2O$) were used as internal standards. Chemical shifts (in ppm) are reported along with peak muliplicities: br (broad), m (multiplet), t (triplet), d (doublet), s (singlet). Elemental analyses were performed by Atlantic Microlab Ind. Norcross, Ga.

Experimental Procedures

A. Dibenzyl Iminodiacetate (1)

A mixture of iminodiacetic acid (16.64 g, 0.125 mol), toluenesulfonic acid (28.5 g, 0.15 mol), and 60 ml of benzyl alcohol in 100 ml benzene was refluxed for 24 h with continuous removal of water using a Dean-Stark trap. After addition of ether to the cooled reaction mixture, toluenesulfonate salt of the benzylated iminodiacetate was obtained as a solid. Subsequently, triethylamine (25 ml) was added to a suspension of the toluenesulfonate salt in ethyl acetate and stirred for 30 minutes. The ethyl acetate solution was washed with water, dried with $MgSO_4$, filtered and concentrated under reduced pressure affording 35.7 g (91%) of compound 1 used for the next reaction step without further purification. NMR ($CDCl_3$):1.4–2.2 (br s,1H), 3.52 (s,4H), 7.35 (s,10H).

B. N,N-Bis(benzyloxycarbonylmethyl)bromoacetamide (2)

A solution of dibenzyl iminodiacetate (9.7 g, 0.031 mol) and triethylamine (4.05 g, 0.04 mol) in 30 ml of carbon tetrachloride was added dropwise to a solution of bromoacetyl bromide (8.88 g, 0.044 mol in 20 ml of carbon tetrachloride at 0° C., and stirring was continued for 2 h at 25° C. After addition of water, the organic layer was washed with a saturated $NaHCO_3$ solution and saturated brine, dried with $MgSO_4$, filtered and concentrated under reduced pressure. The residue was purified by flash column chromatography [silica gel, hexane:EtAOc (3:1)] and yielded 12.66 g (94%) of compound 2. NMR ($CDCl_3$): 3.86 (s,2H), 4.25 (s,2H), 4.27 (s,2H), 5.15 (s,2H), 5.19 (s,2H), 7.3–7.5 (m,10H). Anal. calcd. for $C_{20}H_{20}BrNO_5$: C, 55.31; H, 4.64; Br, 18.40; N, 3.23. Found: C, 55.38; H, 4.69; Br, 18.46; N, 3.19.

C. N,N-bis(2-hydroxyethyl)-N,N-bis[N',N'-bis-(benzyloxycarbonylmethyl)acetamido]-1,2-ethanediamine (3)

A suspension of N,N-bis(2-hydroxyethyl)-ethanediamine (0.8 g, 0.0054 mol) and triethylamine (1.27 g, 0.012 mol) in 5 mol of DMF was treated with a solution of bromo compound 2 (5.21 g, 0.012 mol) in 5 ml of DMF and stirring was continued for 2 h at room temperature. The reaction mixture was diluted with EtOAc and the organic solution was washed with 0.5N HCl, 0.5N NaOH and saturated brine. The organic layer was concentrated under reduced pressure affording an alkylated intermediate 3 used for the next step without further purification.

D. N,N'-Bis(2-butyroyloxyethyl)-N,N'-bis[N'',N''-bis (benzyloxycarbonylmethyl)acetamido]-1,2 ethanediamine (4)

A solution of compound 3 (0.013 mol) and DMAP (0.026 mol) in 50 ml of dry THF was treated with a solution of butyryl chloride (0.026 mol) in 30 ml of dry THF and the resulting solution was stirred at room temperature overnight. The mixture was diluted with EtOAc and water. The organic layer was washed with a saturated $NaHCO_3$ solution and saturated brine, dried with $MgSO_4$, filtered and concentrated under reduced pressure. Purification [silica gel, hexane:EtOAc (2:1)] afforded 66% of compound 4.

E. N,N'-Bis(2-propionoyloxyethyl)-N,N'-bis[N'',N''- bis(benzyloxycarbonylmethyl)acetamido]-1,2 ethanediamine (5)

A solution of compound 3 (0.013 mol) and DMAP (0.026 mol) in 50 ml of dry THF was treated with a solution of propionyl chloride (0.026 mol in 30 ml of dry THF and the resulting solution was stirred at room temperature overnight. The mixture was diluted with EtOAc and water. The organic layer was washed with a saturated $NaHCO_3$ solution and saturated brine, dried with $MgSO_4$, filtered and concentrated under reduced pressure. Purification [silica gel, hexane:EtOAc (2:1)] afforded 70% of compound 5.

F. N-(2-propionoyloxyethyl)-N'-(2-butyroyloxy- ethyl)-N-N'-bis[N'',N''-bis(benzyloxycarbonylmethyl)acetamido]-1,2 ethanediamine (6)

To a solution of compound 3 (0.007 mol) and DMAP (0.86 g, 0.007 mol) in 10 ml of dry THF, a solution of butyryl chloride (0.007 mol) in 5 ml of dry THF was added dropwise at 0° C., and stirring was continued for 1 h at 0° C. and for 2 h at room temperature. The mixture was diluted with EtOAc and water. The organic layer was washed with a saturated $NaHCO_3$ solution and saturated brine, dried with $MgSO_4$, filtered and concentration under reduced pressure. This "monohydroxyl" intermediate was used for the next step without further purification.

To a solution of the monohydroxy intermediate (0.007 mol) and DMAP (0.86 g, 0.007 mol) in 10 ml of dry THF, a solution of propionyl chloride (0.007 mol) in 5 ml of dry THF was added dropwise at 0° C., and stirring was continued for 1 h at 0° C. and for 2 h at room temperature. The mixture was diluted with EtOAc and water. The organic layer was washed with a saturated $NaHCO_3$ solution and saturated brine, dried with $MgSO_4$, filtered and concentrated under reduced pressure. Purification [silica gel, hexane:EtOAc (2:1)] afforded 50% of compound 6.

G. N-(2-Acetoyloxyethyl)-N'-(2-butyroyloxyethyl)- N,N'-bis[N'',N''-bis(benzyloxycarbonylmethyl) acetamido]-1,2 ethanediamine (7)

To a solution of compound 3 (0.007 mol) and DMAP (0.86 g, 0.007 mol) in 10 ml of dry THF, a solution of butyryl chloride (0.007 mol) in 5 ml of dry THF was added dropwise at 0° C., and stirring was continued for 1 h at 0° C. and for 2 h at room temperature. The mixture was diluted with EtOAc and water. The organic layer was washed with a saturated $NaHCO_3$ solution and saturated brine, dried with $MgSO_4$, filtered and concentrated under reduced pressure. This "monohydroxy" intermediate was used for the next step without further purification.

To a solution of the monohydroxy intermediate (0.007 mol) and DMAP (0.86 g, 0.007 mol) in 10 ml of dry THF, a solution of acetyl chloride (0.007 mol) in 5 ml of dry THF was added dropwise at 0° C., and stirring was continued for 1 h at 0° C. and for 2 h at room temperature. The mixture was diluted with EtOAc and water. The organic layer was washed with a saturated $NaHCO_3$ solution and saturated brine, dried with $MgSO_4$, filtered and concentrated under reduced pressure. Purification [silica gel, hexane:EtOAc (2:1)] afforded 55% of compound 7.

H. General Procedure for the Catalytic Hydrogenation Used for the Synthesis of Compounds 8, 9, 10 and 11

Solutions of compounds 4, (0.220 g), 5 (0.233 g), 6 (0.100 g) and 7 (2.909 g) in 50 ml of ethanol were hydrogenated over 10% palladium on carbon at 60 psi overnight. The reaction solutions were filtered and concentrated under reduced pressure. The residues were recrystallized from isopropanol affording 50–70% of compounds 8 (0.110 g, 50%), 9 (0.140 g, 60%), 10 (0.080 g, 80%) and 11 (1.623 g, 69%)

N,N'-Bis(2-butyroyloxyethyl)-N,N'-bis[N",N"- bis (carboxylmethyl)acetamido]-1,2 ethanediamine (BBE-DTTA) (8). $^1$H NMR [D$_2$O, reference 3- (trimethylsilyl) -1-propane-sulfonic acid, sodium salt(TSP)]: 0.91 (t,6H), 1.59–1.64 (m,4H), 2.40 (t,4H), 3.28 (s,4H), 3.37 (s,4H), 4.06 (s,4H), 4.18 (s,8H), 4.34 (s,4H), 12.95 (bs,4H).

N,N'-Bis(2-propionoyloxyethyl)-N,N'- bis[N",N"-bis (carboxylmethyl)acetamido]-1,2 ethanediamine (BPE-DTTA) (9). $^1$H NMR [D$_2$O, reference 3-(trimethylsilyl)-1-propane-sulfonic acid, sodium salt(TSP)]: 1.08 (t,6H), 2.42 (q,4H), 3.28 (s,4H), 3.37 (s,4H), 4.06 (s,4H), 4.18 (s,4H), 4.34 (s,4H), 12.95 (bs,4H).

N- (2-propionoyloxyethyl) -N'- (2-butyroyloxy- ethyl)-N-N'-bis[N",N"-bis(carboxylmethyl)acetamido]- 1,2 ethanediamine (PBE-DTTA) (10). $^1$H NMR [D$_2$O, reference 3-(trimethylsilyl)-1-propane-sulfonic acid, sodium salt (TSP)]:

N-(2-acetoyloxyethyl)-N'-(2-butyroyloxy- ethyl)-N,N'-bis[N",N"-bis(carboxylmethyl)-acetamido]- 1,2 ethanediamine (ABE-DTTA) (11). $^1$H NMR [D$_2$O, reference 3-(trimethylsilyl)-1-propane-sulfonic acid, sodium salt (TSP)]: 0.90 (t,3H), 1.59–1.64 (m,2H), 2.11 (s,3H), 2.40 (t,2H), 3.28 (s,4H), 3.37 (s,4H), 4.06 (s,4H), 4.18 (s,8H), 4.34 (s,4H), 12.95 (bs,4H). MS(M+1):607.00.

EXAMPLE 2

A. Preparation of Gd(ABE-DTTA)

A water-soluble, lipophilic contrast-enhancing agent of the present invention was prepared as described hereinbelow. Specifically, the water-soluble contrast-enhancing agent was prepared by dissolving 0.12 g (1.98×10$^{-4}$ mole, MW 606.58 g/mole) of ABE-DTTA in a 3 ml saline buffer which comprised 0.9% NaCl and 20 mM of N-[2-hydroxyethyl]piperazine- N$^1$-[2-ethanesulfonic acid] (HEPES). The pH of the solution was about 8.06.

An aliquot containing 1.16×10$^{-4}$ mole of GdCl$_3$ was diluted to 1 ml by adding 0.65 ml saline and 20 mM HEPES. This aliquot was then added dropwise to the ABE-DTTA solution with strong vortexing. The pH of the solution after addition was 1.98 and the resulting solution was clear. The pH of the solution was then adjusted to 5.87 using the above buffer solution. Another 0.35 equivalent of the ABE-DTTA solution was added into the solution which brought the ligand/metal ratio to 1.75 and the pH of the solution to 4.28. Heavy precipitation emerged when the pH was adjusted to 6.57. The precipitated solution was then diluted to a total 50 ml which generated a clear solution. The final solution had a pH of 7.31 and a Gd(ABE-DTTA) concentration of 2.3 mM.

The average T$_1$ values at 10 MHZ of the Gd(ABE-DTTA) solution prepared above adjusted to 1 mM was 0.04 ms. Thus, the relativity of this agent was $\rho_1$=25.2 s$^{-1}$ (mmol/L)$^{-1}$.

B. Cardiac Tissue Imaging and Analysis

In this experiment, male ferrets weighing about 0.9–1.2 Kg (Marshall Farrs) were anesthetized with sodium pentobarbital (25 mg/Kg). A tracheal tube was inserted and connected to a respirator (intermediate animal ventilator, Harvard Apparatus, Inc.) with a setting for 45 ml tidal volume at a rate of about 25 cycles per minute. The left jugular vein was isolated and an intravenous (IV) line was inserted to allow the administration of infusion and the contrast agent. The left carotid artery was instrumented for blood pressure and the ECG was recorded.

A 1.5 Tesla Philips Gyroscan with a head coil was used for ferret heart imaging. An ECG gated, relatively T$_1$ weighted (TR=600 ms, TE=30 ms), spin echo pulse sequence was set up in a multiple slice, multiple phase, dynamic study. During the ten minutes of each dynamic interval, nine images with three tomographic slices in three cardiac phases (two diastolic and one systolic phase) were obtained. Control images were obtained, and subsequently thereafter a bolus of 50 μmol/Kg of water-soluble Gd(ABE-DTTA) was injected, and the MRI signal intensity enhancement was monitored over a 3 hour interval.

In these experiments, an agarose phantom in a plastic cup was used as an external intensity reference. In traverse myocardial slices (short axis, dual chamber view) septal, anterior, lateral and posterior segments were selected as regions of interest (ROI's). Average intensity in each ROI was measured and normalized to the intensity of the external reference. The intensity enhancement (IE) in each ROI is expressed herein by the following equation:

$$IE=100\ (I_{post}-I_{pre})/I_{pre}$$

where $I_{pre}=I_{organ}/I_{reference}$ (before injection of said agent), $I_{post}=I_{organ}/I_{reference}$ (after injection of the agent), and I denotes the signal intensity.

The results of this study using Gd(ABE-DTTA) as the water-soluble contrast-enhancing agent are shown in FIG. 1. Specifically, injecting 50 μmol/Kg Gd(ABE-DTTA) induced, within 15 minutes, an MRI IE of 40% which remained in effect for three hours (see FIG. 1). This kinetic behavior is typical of lipophilic agents, e.g. liposomal Gd(BME-DTTA) and thus is quite surprising for a water-soluble agent such as the exemplified in this example. Moreover, these results show that this water-soluble contrast-enhancing agent of the present is effective in imaging heart tissue.

EXAMPLE 3

The water-soluble, lipophilic contrast-enhancing agent, Gd(BAE-DTTA) was prepared in accordance with the procedure of Example 2 except that 0.113 g (1.95×10$^{-4}$ mole, MW 578.5 g/mole) of BAE-DTTA was employed as the complexing acid. The final solution had a pH of 7.21 and a Gd(BAE-DTTA) concentration of 33.3 mM.

The average T$_1$ values at 10 MHZ of the Gd(BAE-DTTA) solution prepared above adjusted to 1 mM was 71.1 ms. Thus, the relaxivity of this agent was $\rho_1$=14.05 s$^{-1}$ (mmol/L)$^{-1}$.

Figure 2:
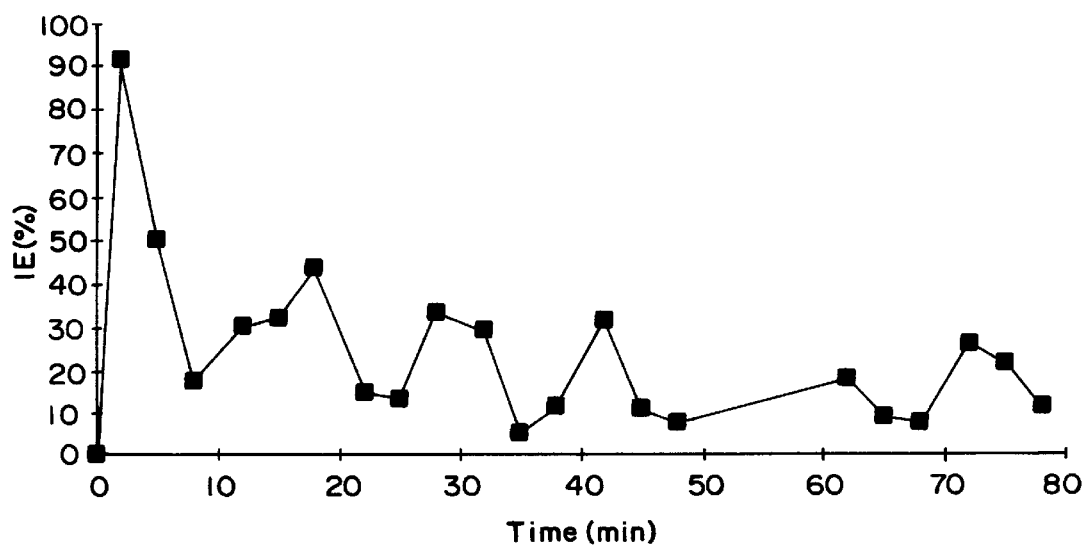
FIG. 2 is a graph of the myocardial proton MRI intensity enhancement, expressed in %, vs. time, expressed in minutes, utilizing Gd(BAE-DTTA) as the contrast-enhancing agent in an in vivo ferret experiment.

Cardiac tissue imaging and analysis was conducted using Gd(BAE-DTTA) as the water-soluble contrast-enhancing agent utilizing the procedure set forth in Example 2. The results of these experiments are shown in FIG. 2. Specifically, FIG. 2 shows that the water-soluble contrast-enhancing agent Gd(BAE-DTTA) induced an MRI IE of 90% in 2 minutes. The MRI IE decreased to 50% at 5 minutes after injection, and gradually diminished. Thus, this agent displayed a Magnevist-like kinetics typical of water-soluble contrast agents which enhance quickly after administration but also clear quickly with not much tissue retention. This behavior or Gd(BAE-DTTA) is in fact not surprising and is quite expected considering its water solubility.

EXAMPLE 4

The water-soluble, lipophilic contrast-enhancing agent, Gd(MHE-DTTA) was prepared in accordance with the procedure of Example 2 except that 0.0846 g ($1.20 \times 10^{-4}$ mole, MW 704.8 g/mole) of MHE-DTTA was employed as the complexing acid. The final solution had a pH of 7.36 and a Gd(MHE-DTTA) concentration of 10.6 mM.

The average $T_1$ values at 10 MHZ of the Gd(MHE-DTTA) solution prepared above adjusted to 1 mM was 73.5 ms. Thus, the relaxivity of this agent was $\rho_1 = 13.6$ s$^{-1}$ (mmol/L)$^{-1}$.

Figure 3:
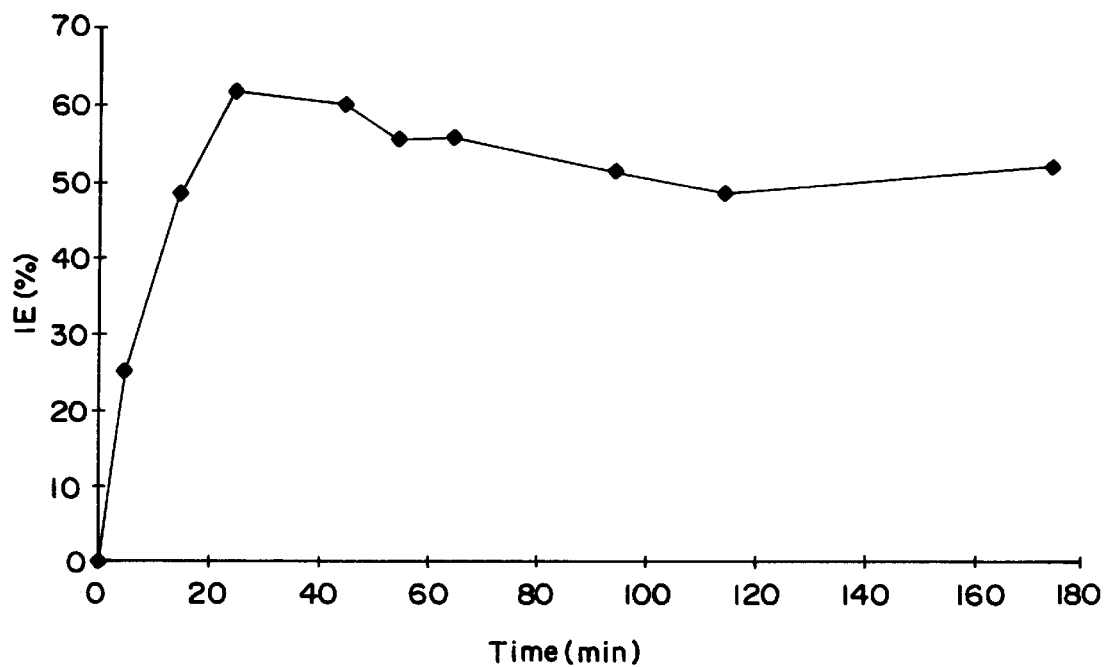
FIG. 3 is a graph of the average myocardial proton MRI intensity enhancement, expressed in %, vs. time, expressed in minutes, utilizing Gd(MHE-DTTA) as the contrast-enhancing agent in five ferrets, in vivo.

Cardiac tissue imaging and analysis was conducted using Gd(MHE-DTTA) as the water-soluble contrast-enhancing agent utilizing the procedure set forth in Example 2. The results of these experiments are shown in FIG. 3. Specifically, FIG. 3 shows that the MRI IE increased to 55±2% reaching this plateau level at about 25 minutes after administration. Thus, this agent behaves like liposomal Gd(BME-DTTA), a lipophilic, non-water soluble agent, and like the water soluble agent Gd(ABE-DTTA).

COMPARATIVE EXAMPLE 1

In this comparative example, the gadolinium complex of $N^3,N^6$-bis(2'-myristoyloxyethyl)-1,8-dioxo-triethylenetetraamine-N,N,N',N'-tetraacetic acid [Gd(BME-DTTA)] was prepared and used for cardiac tissue imaging. Specifically, Gd(BME-DTTA) was synthesized and incorporated into liposomes using the procedure described in the Elgavish et al. article entitled "Fatty-acyl iminopolycarboxylates; lipophilic bifunctional contrast agents for NMR imaging", Magn. Reson. Med. 1991; Vol 22; pp. 57–67.

The liposomal Gd(BME-DTTA) was dialyzed at 4° C. for 24 hours against a saline solution (pH 7.4) that contained 0.9 weight % NaCl, 20 mmol/L HEPES, and 0.5 weight % Chelex-100 to remove any weakly bound Gd ions. The relaxivity of Gd(BME-DTTA) was found to be 27.1±0.3 s$^{-1}$ (mmol/L)$^{-1}$.

Figure 4:
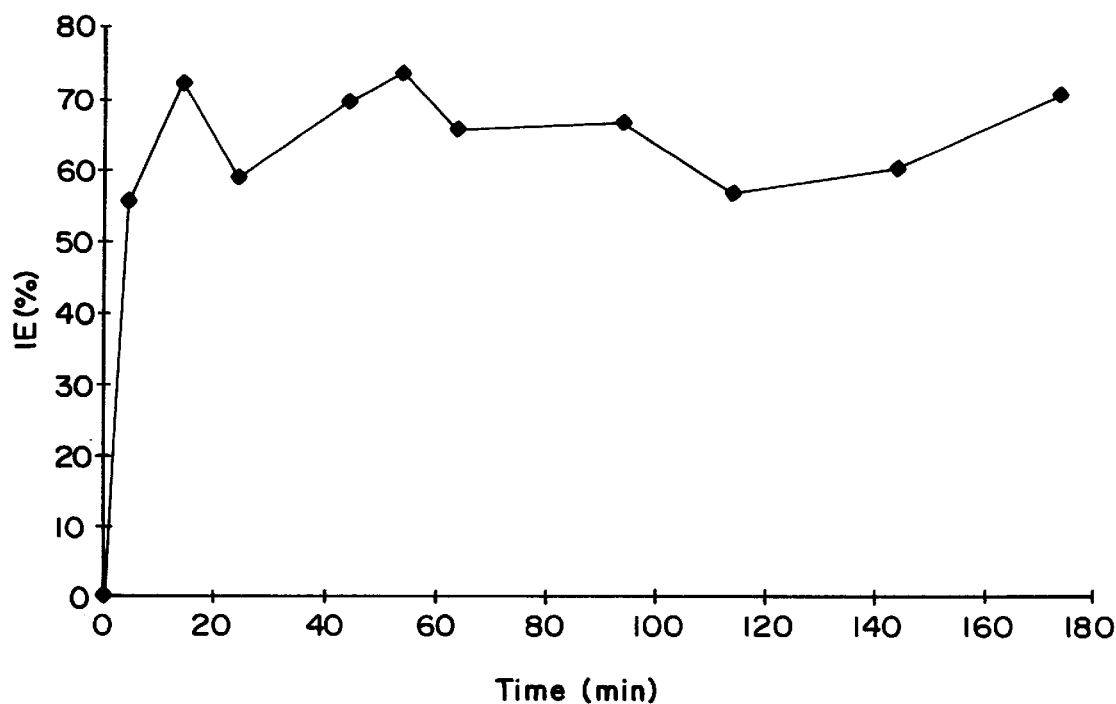
FIG. 4 is a graph of the average myocardial MRI intensity enhancement, expressed in %, vs. time, expressed in minutes, utilizing Gd(BME-DTTA) as the contrast-enhancing agent in six ferrets, in vivo.

The dialyzed, liposomal Gd(BME-DTTA) was then used in cardiac imaging using the procedure described in Example 1. The results of these experiments are shown in FIG. 4 whereat it is shown that the intensity in the heart muscle increased by 65±5% (ρ<0.001) within 15 minutes after administration. Beyond the first hour, the average intensity remained at a plateau level for about 3 hours indicating a reasonably long lifetime of the contrast agent in the heart muscle. It should be emphasized that, among the water-soluble contrast-enhancing agents exemplified in Examples 2–4, the agent of Example 2 is the most viable replacement for the liposomal Gd(BME-DTTA) contrast-enhancing agent. Moreover, it should be noted that the present water-soluble contrast-enhancing agents, such as those described in Examples 2–4, are not placed in liposomes or any other conjugating agent known in the art. Thus, due to their increased water solubility the present contrast-enhancing agents represent an advancement over prior art agents such as Gd(BME-DTTA).

What is claimed is:

1. A water-soluble contrast-enhancing agent comprising a complexing acid or a salt thereof and at least one paramagnetic, diamagnetic or ferromagnetic metal ion, in any stoichiometric ratio between said metal ion and said complexing acid or salt, wherein said complexing acid or salt has the formula:

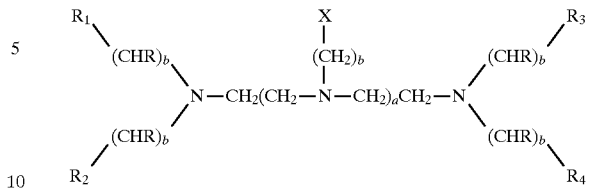

wherein a is 0 to 5; b is 1 to 5; each of a and b can be the same or different; each R is the same or different and is hydrogen, lower alkyl, hydroxy, halo, lower alkoxy, aryl, or lower aralkyl; at least one of $R_1$, $R_2$, $R_3$, $R_4$, or X has the formula:

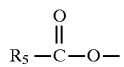

wherein $R_5$ is hydrogen or a saturated or unsaturated, substituted or unsubstituted hydrocarbon chain having less than 6 carbon atoms; and the others of $R_1$, $R_2$, $R_3$, $R_4$, or X are hydrogen, hydroxyl, —COOR$_6$, —CONR$_7$R$_8$ or a chelating moiety, wherein $R_6$, $R_7$ and $R_8$ are the same or different and represent hydrogen, lower alkyl, lower alkoxy, lower carboxyalkylene, a saturated or unsaturated, substituted or unsubstituted hydrocarbon chain having from about 1 to about 30 carbon atoms, or a chelating moiety.

2. The water-soluble contrast-enhancing agent of claim 1 wherein $R_5$ is a hydrocarbon chain substituted with a hydroxyl, lower alkoxy or halogen moiety.

3. The water-soluble contrast enhancing agent of claim 1 wherein said complexing acid has the formula:

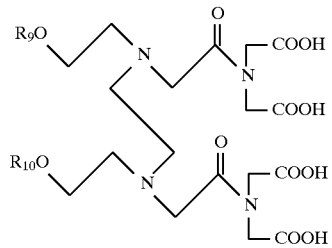

wherein $R_9$ a short chain fatty acyl moiety of the formula:

wherein $R_{11}$ is hydrogen or a saturated or unsaturated, substituted or unsubstituted hydrocarbon chain containing less than 6 carbon atoms and $R_{10}$ is a fatty acyl moiety of the formula:

wherein $R_{12}$ is a saturated or unsaturated, substituted or unsubstituted hydrocarbon chain containing from about 1 to about 30 carbon atoms.

4. The water-soluble contrast-enhancing agent of claim 3 wherein $R_{11}$ is a hydrocarbon chain substituted with a hydroxyl, lower alkoxy or halogen moiety and $R_{12}$ is a hydrocarbon chain substituted with a lower alkyl, hydroxyl, lower alkoxy or halogen moiety.

5. The water-soluble contrast-enhancing agent of claim 3 wherein $R_{12}$ is a hydrocarbon chain substituted with a lower alkyl.

6. The water-soluble contrast-enhancing agent of claim 3 wherein $R_{11}$ is a saturated or unsaturated hydrocarbon containing from about 1 to about 3 carbon atoms and $R_{12}$ is a saturated or unsaturated hydrocarbon chain containing from about 3 to about 29 carbon atoms.

7. The water-soluble contrast-enhancing agent of claim 1 wherein said complexing acid is N-(2- acetoyloxyethyl)-N'-(2-butylroyloxyethyl)-N,N'- bis[N",N"-bis(carboxylmethyl) acetamido]-1,2 ethanediamine(ABE-DTTA), N-(2'-myristoyloxyethyl)-N'-(2'-hydroxyethyl) 1,8-dioxo-triethylenetetraamine- N,N,N',N'-tetraacetic acid (MHE-DTTA), N,N'-bis(2-butyroyloxyethyl)-N,N'-bis[N",N"-bis (carboxylmethyl) acetamido]-1,2 ethanediamine (BBE-DTTA), N,N'-bis(2-propionoyloxyethyl)-N,N'-bis[N",N"-bis(carboxylmethyl) acetamido]-1,2 ethanediamine (BPE-DTTA), N-(2-propionoyloxyethyl)-N'-(2-butyrolyloxyethyl)-N,N'- bis[N",N"-bis(carboxylmethyl)-acetamido]-1,2 ethanediamine (PBE-DTTA) or N,N'-bis(2-acetoyloxy-ethyl)-N,N'-bis[N",N"-bis(carboxylmethyl) acetamido]- 1,2 ethanediamine (BAE-DTTA).

8. The water-soluble contrast-enhancing agent of claim 7 wherein said complexing acid is ABE-DTTA.

9. The water-soluble contrast-enhancing agent of claim 7 wherein said completing acid is MHE-DTTA.

10. The water-soluble contrast-enhancing agent of claim 1 wherein said metal ion is an element with an atomic number 21 to 29, 42 to 44 or 57 to 83.

11. The water-soluble contrast-enhancing agent of claim 10 wherein said metal ion is gadolinium (Gd).

12. A method for diagnostic image analysis comprising:

(i) administering to a host a contrast-enhancing amount of a water-soluble contrast-enhancing agent which comprises a complexing acid or salt thereof and at least one paramagnetic, diamagnetic or ferromagnetic metal ion, in any stoichiometric ratio between said metal ion and said complexing acid, wherein said complexing acid has the formula:

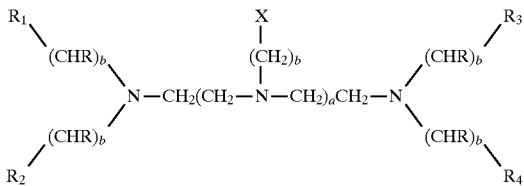

wherein a is 0 to 5; b is 1 to,5; each of a and b can be the same or different; each R is the same or different and is hydrogen, lower alkyl, hydroxy, halo, lower alkoxy, aryl, or lower aralkyl; at least one of $R_1$, $R_2$, $R_3$, $R_4$, or X has the formula:

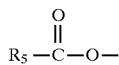

wherein $R_5$ is hydrogen or a saturated or unsaturated, substituted or unsubstituted hydrocarbon chain having less than 6 carbon atoms; and the others of $R_1$, $R_2$, $R_3$, $R_4$, or X are hydrogen, hydroxyl, —COOR$_6$, —CONR$_7$R$_8$ or a chelating moiety, wherein $R_6$, $R_7$ and $R_8$ are the same or different and represent hydrogen, lower alkyl, lower alkoxy, lower carboxyalkylene, a saturated or unsaturated, substituted or unsubstituted hydrocarbon chain having from about 1 to about 30 carbon atoms, or a chelating moiety; and (ii) subjecting the same to diagnostic imaging.

13. The method of claim 12 wherein said analysis is magnetic resonance imaging (MRI), nuclear magnetic resonance (NMR), X-ray or ultrasonic analysis.

14. The method of claim 13 wherein said analysis is MRI analysis or NMR analysis.

15. The method of claim 12 wherein said host is a mammal.

16. The method of claim 14 wherein said MRI or NMR analysis is directed to an organ or a tissue of said host.

17. The method of claim 16 wherein said tissue is a cardiac tissue.

18. The method of claim 16 wherein said organ is a heart, kidney, liver, brain or lung.

19. The method of claim 12 wherein $R_5$ is a hydrocarbon chain substituted with a hydroxyl, lower alkoxy or halogen moiety.

20. The method of claim 12 wherein said complexing acid has the formula:

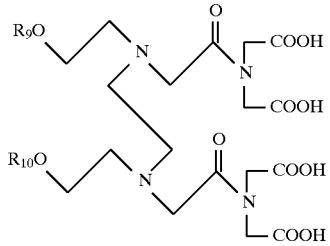

wherein $R_9$ is a short chain fatty acyl moiety of the formula:

wherein $R_{11}$ is hydrogen or a saturated or unsaturated, substituted or unsubstituted hydrocarbon chain containing less than 6 carbon atoms and $R_{10}$ is a fatty acyl moiety of the formula:

wherein $R_{12}$ is a saturated or unsaturated, substituted or unsubstituted hydrocarbon chain containing from about 1 to about 30 carbon atoms.

21. The method of claim 20 wherein $R_{11}$ is a hydrocarbon chain substituted with a hydroxyl, lower alkoxy or halogen moiety and $R_{12}$ is a hydrocarbon chain substituted with a lower alkyl, hvdroxyl, lower alkoxy or halogen moiety.

22. The method of claim 20 wherein $R_{12}$ is a hydrocarbon chain substituted with a lower alkyl.

23. The method of claim 21 wherein $R_{11}$ is a saturated or unsaturated hydrocarbon containing from about 1 to about 3 carbon atoms and $R_{12}$ is a saturated or unsaturated hydrocarbon chain containing from about 3 to about 29 carbon atoms.

24. The method of claim 12 wherein said complexing acid is N-(2-acetoyloxyethyl)-N'-(2- butylroyloxyethyl)-N,N'-bis [N",N"-bis(carboxylmethyl)- acetamido]-1,2 ethanediamine (ABE-DTTA), N-(2'-myristoyloxyethyl)-N'-(2'-hydroxyethyl) 1,8-dioxo- triethylenetetraamine-N,N,N',N'-tetraacetic acid (MHE-DTTA), N,N'-bis(2- butyroyloxyethyl)-N,N'-bis[N'',N''- bis(carboxylmethyl) acetamido]-1,2 ethanediamine (BBE-DTTA), N,N'-bis(2-propionoyl-oxyethyl)-N,N'-bis[N'',N''- bis(carboxylmethyl) acetamido]-1,2 ethanediamine (BPE-DTTA), N-(2-propionoyloxyethyl)-N'-(2-butyrolyloxy- ethyl)-N,N'-bis[N'',N''-bis(carboxylmethyl)-acetamido]- 1,2 ethanediamine (PBE-DTTA) or N,N'-bis(2-acetoyloxyethyl)-N,N'-bis[N'',N''-bis(carboxylmethyl)acetamido]- 1,2 ethanediamine (BAE-DTTA).

25. The method of claim 24 wherein said complexing acid is ABE-DTTA.

26. The method of claim 24 wherein said completing acid is MHE-DTTA.

27. The method of claim 12 wherein said metal ion is an element with an atomic number 21 to 29, 42 to 44 or 57 to 83.

28. The method of claim 27 wherein said metal ion is gadolinium (Gd).

29. The method of claim 12 wherein said contrast-enhancing amount is from about 0.001 mmole to about 5 mmole of said agent per kilogram of said host.

30. A pharmaceutical composition comprising a water-soluble contrast-enhancing agent which is a complexing acid or a pharmaceutically acceptable salt thereof and at least one paramagnetic, diamagnetic or ferromagnetic metal ion, in any stoichiometric ratio between said metal ion and said complexing acid, and, a pharmaceutically acceptable carrier, wherein said complexing acid has the formula:

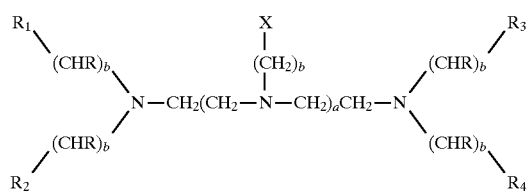

wherein a is 0 to 5; b is 1 to 5; each of a and b can be the same or different; each R is the same or different and is hydrogen, lower alkyl, hydroxy, halo, lower alkoxy, aryl, or lower aralkyl; at least one of $R_1$, $R_2$, $R_3$, $R_4$, or X has the formula:

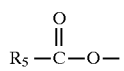

wherein $R_5$ is hydrogen or a saturated or unsaturated, substituted or unsubstituted hydrocarbon chain having less than 6 carbon atoms; and the others of $R_1$, $R_2$, $R_3$, $R_4$, or X are hydrogen, hydroxyl, —$COOR_6$, —$CONR_7R_8$ or a chelating moiety, wherein $R_6$, $R_7$ and $R_8$ are the same or different and represent hydrogen, lower alkyl, lower alkoxy, lower carboxyalkylene, a saturated or unsaturated, substituted or unsubstituted hydrocarbon chain having from about 1 to about 30 carbon atoms, or a chelating moiety.

31. The pharmaceutical composition of claim 30 wherein $R_5$ is a hydrocarbon chain substituted with a hydroxyl, lower alkoxy or halogen moiety.

32. The pharmaceutical composition of claim 30 wherein said complexing acid has the formula:

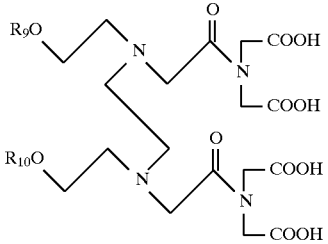

wherein $R_9$ is a short chain fatty acyl moiety of the formula:

wherein $R_{11}$ is hydrogen or a saturated or unsaturated, substituted or unsubstituted hydrocarbon chain containing less than 6 carbon atoms and $R_{10}$ is a fatty acyl moiety of the formula:

wherein $R_{12}$ is a saturated or unsaturated, substituted or unsubstituted hydrocarbon chain containing from about 1 to about 30 carbon atoms.

33. The pharmaceutical composition of claim 32 wherein $R_{11}$ is a hydrocarbon chain substituted with a hydroxyl, lower alkoxy or halogen moiety and $R_{12}$ is a hydrocarbon chain substituted with a lower alkyl, hydroxyl, lower alkoxy or halogen moiety.

34. The pharmaceutical composition of claim 33 wherein $R_{12}$ is a hydrocarbon chain substituted with a lower alkyl.

35. The pharmaceutical composition of claim 33 wherein $R_{11}$ is hydrogen or a saturated or unsaturated hydrocarbon containing from about 1 to about 3 carbon atoms and $R_{12}$ is a saturated or unsaturated hydrocarbon chain containing from about 3 to about 29 carbon atoms.

36. The pharmaceutical composition of claim 30 wherein said completing acid is is N-(2-acetoyloxyethyl)-N'-(2-butylroyloxyethyl)-N,N'-bis[N'',N''- bis(carboxylmethyl)-acetamido]-1,2 ethanediamine (ABE-DTTA), N-(2'-myristoyloxyethyl)-N'-(2'-hydroxyethyl) 1,8-dioxo-triethylenetetraamine-N,N,N',N'-tetraacetic acid (MHE-DTTA), N,N'-bis(2-butyroyloxyethyl) -N,N'-bis[(N'',N''-bis (carboxylmethyl)acetamido]-1,2 ethanediamine (BBE-DTTA), N,N'-bis(2-propionoyloxyethyl)-N,N'-bis[N'',N''-bis(carboxylmethyl) acetamido]-1,2 ethanediamine (BPE-DTTA), N-(2-propionoyloxyethyl)-N'-(2-butyrolyloxyethyl)-N,N'- bis[N'',N''-bis(carboxylmethyl) acetamido]-1,2 ethanediamine (PBE-DTTA) or N,N'-bis(2-acetoyloxyethyl)-N,N'-bis[N'',N''-bis(carboxylmethyl) acetamido]- 1,2 ethanediamine (BAE-DTTA).

37. The pharmaceutical composition of claim 36 wherein said complexing acid is ABE-DTTA.

38. The pharmaceutical composition of claim 36 wherein said completing acid is MHE-DTTA.

39. The pharmaceutical composition of claim 30 wherein said metal ion is an element with an atomic number 21 to 29, 42 to 44 or 57 to 83.

40. The pharmaceutical composition of claim 39 wherein said metal ion is gadolinium (Gd).

41. The pharmaceutical composition of claim 30 wherein said water-soluble contrast-enhancing agent is present in an amount to provide an effective dose of about 0.001 to about 5 mmole of said agent per kilogram of said host.

42. The pharmaceutical composition of claim 30 wherein said pharmaceutically acceptable carrier is a solvent, dispersion media, coating, antibacterial agent, antifungal agent or isotonic agent.

* * * * *

UNITED STATES PATENT AND TRADEMARK OFFICE
CERTIFICATE OF CORRECTION

PATENT NO. : 5,804,164
DATED : September 8, 1998
INVENTOR(S) : Gabriel A. Elgavish It is certified that error appears in the above-identified patent and that said Letters Patent are hereby corrected as shown below:

Column 5, Line 65: "completing" should read --complexing--

Column 21, line 51, Claim 12: "to, 5" should read --to 5--

Column 23, Line 14, Claim 26: "completing" should read --complexing--

Column 24, Line 46, Claim 36: "completing" should read --complexing--

Column 24, line 64, Claim 38: "completing" should read --complexing--

Signed and Sealed this

Twenty-ninth Day of May, 2001

Attest:

NICHOLAS P. GODICI

*Attesting Officer*    *Acting Director of the United States Patent and Trademark Office*